United States Patent
Doering

(10) Patent No.: US 9,861,572 B2
(45) Date of Patent: Jan. 9, 2018

(54) WATER-FREE OIL/THICKENING MIXTURES AS A BASIS FOR COSMETIC SOFT SOLID AND/OR STICK PREPARATIONS

(71) Applicant: Henkel AG & Co. KGaA, Duesseldorf (DE)

(72) Inventor: Thomas Doering, Dormagen (DE)

(73) Assignee: Henkel AG & Co. KGaA (DE)

( * ) Notice: Subject to any disclaimer, the term of this patent is extended or adjusted under 35 U.S.C. 154(b) by 0 days.

(21) Appl. No.: 15/009,504

(22) Filed: Jan. 28, 2016

(65) Prior Publication Data

US 2016/0143839 A1    May 26, 2016

Related U.S. Application Data

(63) Continuation of application No. PCT/DE2014/200284, filed on Jun. 26, 2014.

(30) Foreign Application Priority Data

Jul. 30, 2013   (DE) .................. 10 2013 214 938

(51) Int. Cl.
| | | |
|---|---|---|
| *A61K 8/891* | (2006.01) | |
| *A61K 8/26* | (2006.01) | |
| *A61K 8/34* | (2006.01) | |
| *A61K 8/41* | (2006.01) | |
| *A61K 8/58* | (2006.01) | |
| *A61Q 15/00* | (2006.01) | |
| *A61K 8/02* | (2006.01) | |
| *A61K 8/37* | (2006.01) | |

(52) U.S. Cl.
CPC ............ *A61K 8/891* (2013.01); *A61K 8/0216* (2013.01); *A61K 8/0229* (2013.01); *A61K 8/26* (2013.01); *A61K 8/342* (2013.01); *A61K 8/375* (2013.01); *A61K 8/416* (2013.01); *A61K 8/585* (2013.01); *A61Q 15/00* (2013.01); *A61K 2800/31* (2013.01)

(58) Field of Classification Search
None
See application file for complete search history.

(56) References Cited

U.S. PATENT DOCUMENTS

| | | |
|---|---|---|
| 2,571,030 A | 10/1951 | Govett et al. |
| 4,017,599 A | 4/1977 | Rubino |
| 4,526,780 A * | 7/1985 | Marschner ............... A61K 8/28 |
| | | 424/65 |
| 4,775,528 A | 10/1988 | Callaghan et al. |
| 5,160,454 A | 11/1992 | Knudson, Jr. et al. |
| 5,643,558 A | 7/1997 | Provancal et al. |
| 6,010,688 A | 1/2000 | Shen |
| 6,042,816 A | 3/2000 | Shen |
| 6,245,325 B1 | 6/2001 | Shen |
| 6,663,854 B1 | 12/2003 | Shen et al. |
| 6,902,723 B2 | 6/2005 | Shen |
| 7,105,691 B2 | 9/2006 | Holerca et al. |
| 2004/0009133 A1 | 1/2004 | Kolodzik et al. |
| 2013/0136710 A1 * | 5/2013 | Ge ......................... A61K 8/19 |
| | | 424/65 |

FOREIGN PATENT DOCUMENTS

| | | |
|---|---|---|
| DE | 19756454 C1 | 6/1999 |
| DE | 10333245 A1 | 7/2005 |
| DE | 102004011968 A1 | 9/2005 |
| EP | 011707 A2 * | 8/1984 |
| EP | 0117070 A2 | 8/1984 |
| EP | 011707 A2 * | 2/2001 |
| GB | 1487812 | 10/1977 |
| GB | 2048229 A | 12/1980 |
| WO | 97/17942 A1 | 5/1997 |
| WO | WO 97/17942 * | 5/1997 |

OTHER PUBLICATIONS

PCT International Search Report (PCT/DE2014/200284) dated Oct. 17, 2014.

* cited by examiner

*Primary Examiner* — Robert A Wax
*Assistant Examiner* — Quanglong Truong
(74) *Attorney, Agent, or Firm* — P. Scott Smith

(57) ABSTRACT

The invention relates to water-free compositions, having: at least one oil, and a combination of thickeners, including: a) at least one silicone elastomer, b) at least one straight-chained or branched, saturated or unsaturated alcohol having more than 18 carbon atoms, and c) at least one clay mineral mixture modified with quaternary ammonium compounds. The water-free compositions are suitable in particular as soft solid preparations for use on the human skin. In particular, the compositions are suitable as a soft solid antiperspirant composition.

17 Claims, No Drawings

WATER-FREE OIL/THICKENING MIXTURES AS A BASIS FOR COSMETIC SOFT SOLID AND/OR STICK PREPARATIONS

FIELD OF THE INVENTION

The present invention generally relates to anhydrous compositions including a specific combination of thickening agents, in addition to an oil. The invention further relates to the use of oil/thickening agent mixtures as a basis for cosmetic soft solid and/or stick preparations.

BACKGROUND OF THE INVENTION

Cosmetic stick preparations, such as lipsticks or deodorant sticks, have been known for quite some time and are used regularly by many consumers in the widest fields of body care.

However, they may have the disadvantage that they are perceived as being too hard when applied to the skin. Other problematic aspects are at times the dosing of the products and the undesirable tendency of some stick preparations to form residues on the application surface.

For these reasons, what are known as "soft solids" were developed as a further form of application, which are perceived to be more pleasant by many consumers than stick preparations.

"Soft solids" are understood to mean viscous compositions that typically have a creamy texture and, prior to use, are usually pushed out through one or more openings of a dispensing device of the applicator. During this process, pressure is exerted on the composition, under which the formulation often becomes unstable and expels one of the liquid components thereof. This phenomenon is referred to as syneresis and can typically be observed with soft solids having a high oil content.

Products that exhibit syneresis of >8% at 50° C. are already problematic and undesirable.

Anhydrous soft solids and anhydrous stick preparations typically include suspensions of one (or more) auxiliary substance(s) and/or active ingredient(s) in a nonpolar oil, which includes at least one thickening agent to prevent sedimentation of the auxiliary substance(s) and/or active ingredient(s). It was found that multiple commercially known thickening agents (thickening agent systems) favor this undesirable syneresis, in particular when the preparations, as described above, are pushed out of the applicator by the exertion of pressure (soft solids).

It was therefore the object of the present invention to provide a cosmetic composition in the form of an anhydrous composition as a soft solid, which exhibits no, or at least reduced, syneresis. Moreover, the composition is to have the necessary hardness and texture so as to be easily distributed on the skin.

A necessary hardness shall preferably be understood to mean a hardness of 0.015 to 0.045 mN, more preferably of 0.016 to 0.044 mN, particularly preferably of 0.017 to 0.043 mN, and in particular of 0.018 to 0.042 mN.

Reduced syneresis shall preferably be understood to mean syneresis of <7.5%, more preferably <7.25%, particularly preferably <7%, and in particular <6.75%.

Finally, the composition should not leave behind a sticky sensation on the skin and no residues on textiles after application.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

An anhydrous composition, comprising: at least one oil; and a combination of thickening agents, comprising: at least one silicone elastomer; at least one straight-chain or branched, saturated or unsaturated alcohol having more than 18 carbon atoms; and at least one clay mineral mixture modified with quaternary ammonium compounds.

Use of mixtures comprising: at least one oil; and a combination of thickening agents, comprising: at least one silicone elastomer; at least one straight-chain or branched, saturated or unsaturated alcohol having more than 18 carbon atoms; and at least one clay mineral mixture modified with quaternary ammonium compounds, as a basis for cosmetic soft solid and/or stick preparations.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It was found that the stated object is achieved by the following first subject matter of the invention: an anhydrous composition, comprising:
at least one oil; and
a combination of thickening agents, comprising:
 a) at least one silicone elastomer;
 b) at least one straight-chain or branched, saturated or unsaturated alcohol having more than 18 carbon atoms; and
 c) at least one clay mineral mixture modified with quaternary ammonium compounds.

All information regarding the states of matter of the starting materials used (solid, liquid, and the like) in this application refer to normal conditions. "Normal conditions" within the meaning of the present application refer to a temperature of 20° C. and a pressure of 1013.25 mbar. Melting point information likewise refers to a pressure of 1013.25 mbar.

The term "anhydrous" according to the invention shall be understood such that the compositions include 0 to a maximum of 3 wt. %, preferably 0 to a maximum of 2 wt. %, free water, based on the total composition. The content of constitutional water, hydration water or similarly molecularly bound water that can be present in the components used, in particular in optionally present active antiperspirant ingredients, does not constitute free water within the meaning of the present application.

The anhydrous compositions according to the invention are generally suitable for all cosmetic forms of application in which soft solids and/or stick preparations are customarily used (for example, lipsticks, soft solid lip care formulations, balm and/or soft solid formulations for the skin, antiperspirants, and the like).

In a preferred embodiment, however, the anhydrous compositions according to the invention are formulated as soft solids and used in particular as antiperspirants.

Anhydrous compositions according to the invention that are used as antiperspirants additionally include at least one active antiperspirant ingredient (which is also referred to as an active perspiration-inhibiting ingredient).

The active antiperspirant ingredient is preferably used in the anhydrous compositions according to the invention that are used as antiperspirants in an amount of 3 to 35 wt. %, more preferably 5 to 30 wt. %, and particularly preferably 10 to 25 wt. %, wherein the amounts refer to the total weight of the constitutional water-free active substance (USP) in the total composition.

Preferred active antiperspirant ingredients are selected from the water-soluble astringent inorganic and organic aluminum, zirconium and zinc salts, and arbitrary mixtures of these salts.

According to the invention, water solubility shall be understood to mean a solubility of at least 5 wt. % at 20° C., which is to say that amounts of at least 5 g of the active antiperspirant ingredient are soluble in 95 g water at 20° C.

Particularly preferred active antiperspirant ingredients are selected from aluminum chlorohydrate, in particular aluminum chlorohydrate of general formula $[Al_2(OH)_5Clx1\text{-}6H_2O]_n$, preferably $[Al_2(OH)_5Clx2\text{-}3H_2O]_n$, which may be present in non-activated or in activated (depolymerized) form, and aluminum chlorohydrate of general formula $[Al_2(OH)_4Cl_2x1\text{-}6H_2O]_n$, preferably $[Al_2(OH)_4Cl_2x2\text{-}3H_2O]_n$, which may be present in non-activated or in activated (depolymerized) form.

The production of preferred active antiperspirant ingredients is disclosed in U.S. Pat. No. 3,887,692, U.S. Pat. No. 3,904,741, U.S. Pat. No. 4,359,456, GB 2048229, and GB 1347950, for example.

Furthermore preferred are aluminum sesquichlorohydrate, aluminum dichlorohydrate, aluminum chlorohydrex propylene glycol (PG) or aluminum chlorohydrex polyethylene glycol (PEG), aluminum or aluminum-zirconium glycol complexes, such as aluminum or aluminum-zirconium propylene glycol complexes, aluminum sesquichlorohydrex PG or aluminum sesquichlorohydrex PEG, aluminum dichlorohydrex PG or aluminum dichlorohydrex PEG, aluminum hydroxide, furthermore selected from the aluminum-zirconium chlorohydrates, such as aluminum-zirconium trichlorohydrate, aluminum-zirconium tetrachlorohydrate, aluminum-zirconium pentachlorohydrate, aluminum-zirconium octachlorohydrate, the aluminum-zirconium chlorohydrate glycine complexes, such as aluminum-zirconium trichlorohydrex glycine, aluminum-zirconium tetrachlorohydrex glycine, aluminum-zirconium pentachlorohydrex glycine, aluminum-zirconium octachlorohydrex glycine, potassium aluminum sulfate ($KAl(SO_4)_2x12H_2O$, alum), aluminum undecylenoyl collagen amino acid, sodium aluminum lactate+aluminum sulfate, sodium aluminum chlorohydroxy lactate, aluminum bromohydrate, aluminum chloride, the complexes of zinc and sodium salts, the complexes of lanthanum and cerium, the aluminum salts of lipoamino acids, aluminum sulfate, aluminum lactate, aluminum chlorohydroxy allantoinate, sodium aluminum chlorohydroxy lactate, zinc chloride, zinc sulfocarbolate, zinc sulfate, zirconyl oxyhalides, in particular zirconyl oxychlorides, zirconyl hydroxy halides, in particular zirconyl hydroxy chlorides (zirconium chlorohydrate).

Particularly preferred active antiperspirant ingredients according to the invention are selected from what are known as "activated" aluminum and aluminum-zirconium salts, which are also referred to as enhanced-activity active antiperspirant ingredients. Such active ingredients are known from the prior art and are also commercially available. Production of the same is disclosed in GB 2048229, U.S. Pat. No. 4,775,528, and U.S. Pat. No. 6,010,688. Activated aluminum and aluminum-zirconium salts are generally produced by heat treating a relatively dilute solution of the salt (such as approximately 10 wt. % salt), so as to increase the HPLC peak 4 to peak 3 area ratio of the same. The activated salt can subsequently be dried to obtain a powder, in particular spray-dried. In addition to spray drying, drum drying also suited, for example.

For example, preferred are compositions that comprise, in percent by weight (USP): 18 to 45 wt. % of an activated aluminum or aluminum-zirconium salt, 55 to 82 wt. % of at least one anhydrous polyhydric alcohol comprising 3 to 6 carbon atoms and 3 to 6 hydroxyl groups, preferably propylene glycol, butylene glycol, diethylene glycol, dipropylene glycol, glycerol, sorbitol and pentaerythritol, particularly preferably propylene glycol.

Particularly preferred are also complexes of activated antiperspirant aluminum or aluminum-zirconium salts, comprising a polyhydric alcohol, which include 20 to 50 wt. %, particularly preferably 20 to 42 wt. %, activated antiperspirant aluminum or aluminum-zirconium salt and 2 to 16 wt. % molecularly bound water, wherein the remainder to make up to 100 wt. % is at least one polyhydric alcohol comprising 3 to 6 carbon atoms and 3 to 6 hydroxyl groups. Propylene glycol, propylene glycol/sorbitol mixtures, and propylene glycol/pentaerythritol mixtures are preferred such alcohols. Such preferred complexes according to the invention of an activated antiperspirant aluminum or aluminum-zirconium salt including a polyhydric alcohol are disclosed in U.S. Pat. No. 5,643,558 and U.S. Pat. No. 6,245,325, for example.

Further preferred active antiperspirant ingredients are alkaline calcium-aluminum salts, as they are disclosed in U.S. Pat. No. 2,571,030, for example. These salts are produced by reacting calcium carbonate with aluminum chlorhydroxide or aluminum chloride and aluminum powder, or by adding calcium chloride dihydrate to aluminum chlorhydroxide.

Further preferred active antiperspirant ingredients are aluminum-zirconium complexes, as they are disclosed in U.S. Pat. No. 4,017,599, for example, which are buffered with salts of amino acids, in particular with alkali and alkaline earth glycinates.

Further preferred active antiperspirant ingredients are activated aluminum or aluminum-zirconium salts, as they are disclosed in U.S. Pat. No. 6,245,325 or U.S. Pat. No. 6,042,816, for example, comprising 5 to 78 wt. % (USP) of an activated antiperspirant aluminum or aluminum-zirconium salt, an amino acid or hydroxyalkanoic acid in such an amount so as to provide an (amino acid or hydroxyalkanoic acid) to (Al+Zr) weight ratio of 2:1 to 1:20, and preferably 1:1 to 1:10, and a water-soluble calcium salt in such an amount so as to provide a Ca:(Al+Zr) weight ratio of 1:1 to 1:28, and preferably 1:2 to 1:25. Particularly preferred solid activated antiperspirant salt compositions, for example according to U.S. Pat. No. 6,245,325 or U.S. Pat. No. 6,042,816, include 48 to 78 wt. % (USP), preferably 66 to 75 wt. %, of an activated aluminum or aluminum-zirconium salt and 1 to 16 wt. %, preferably 4 to 13 wt. %, molecularly bound water (hydration water), furthermore an amount of water-soluble calcium salt that is such that the Ca:(Al+Zr) weight ratio is 1:1 to 1:28, preferably 1:2 to 1:25, and an amount of amino acid that is such that the amino acid to (Al+Zr) weight ratio is 2:1 to 1:20, preferably 1:1 to 1:10.

Further particularly preferred solid activated antiperspirant salt compositions, for example according to U.S. Pat. No. 6,245,325 or U.S. Pat. No. 6,042,816, include 48 to 78 wt. % (USP), preferably 66 to 75 wt. %, of an activated aluminum or aluminum-zirconium salt and 1 to 16 wt. %, preferably 4 to 13 wt. %, molecularly bound water (hydration water), furthermore an amount of water-soluble calcium salt that is such that the Ca:(Al+Zr) weight ratio is 1:1 to 1:28, preferably 1:2 to 1:25, and an amount of glycine that is such that the glycine to (Al+Zr) weight ratio is 2:1 to 1:20, preferably 1:1 to 1:10.

Further particularly preferred solid activated antiperspirant salt compositions, for example according to U.S. Pat. No. 6,245,325 or U.S. Pat. No. 6,042,816, include 48 to 78 wt. % (USP), preferably 66 to 75 wt. %, of an activated aluminum or aluminum-zirconium salt and 1 to 16 wt. %, preferably 4 to 13 wt. %, molecularly bound water, furthermore an amount of water-soluble calcium salt that is such that the Ca:(Al+Zr) weight ratio is 1:1 to 1:28, preferably 1:2 to 1:25, and an amount of hydroxyalkanoic acid that is such that the hydroxyalkanoic acid to (Al+Zr) weight ratio is 2:1 to 1:20, preferably 1:1 to 1:10. Preferred water-soluble calcium salts for stabilizing the antiperspirant salts are selected from the group consisting of calcium chloride, calcium bromide, calcium nitrate, calcium citrate, calcium formiate, calcium acetate, calcium gluconate, calcium ascorbate, calcium lactate, calcium glycinate, calcium carbonate, calcium sulfate, calcium hydroxide, and mixtures thereof.

Amino acids that are preferred for the stabilization of the antiperspirant salts are selected from the group consisting of glycine, alanine, leucine, isoleucine, β-alanine, valine, cysteine, serine, tryptophan, phenylalanine, methionine, β-amino-n-butyric acid and γ-amino-n-butyric acid, and the salts thereof, each in the D form, the L form, and the DL form, glycine being particularly preferred.

Hydroxyalkanoic acids that are preferred for the stabilization of the antiperspirant salts are selected from glycolic acid and lactic acid.

Further preferred active antiperspirant ingredients are activated aluminum or aluminum-zirconium salts, as they are disclosed in U.S. Pat. No. 6,902,723, for example, comprising 5 to 78 wt. % (USP) of an activated antiperspirant aluminum or aluminum-zirconium salt, an amino acid or hydroxyalkanoic acid in such an amount so as to provide an (amino acid or hydroxyalkanoic acid) to (Al+Zr) weight ratio of 2:1 to 1:20, and preferably 1:1 to 1:10, and a water-soluble strontium salt in such an amount so as to provide a Sr:(Al+Zr) weight ratio of 1:1 to 1:28, and preferably 1:2 to 1:25.

Particularly preferred solid activated antiperspirant salt compositions, for example according to U.S. Pat. No. 6,902,723, include 48 to 78 wt. % (USP), preferably 66 to 75 wt. %, of an activated aluminum or aluminum-zirconium salt and 1 to 16 wt. %, preferably 4 to 13 wt. %, molecularly bound water, furthermore an amount of water-soluble strontium salt that is such that the Sr:(Al+Zr) weight ratio is 1:1 to 1:28, preferably 1:2 to 1:25, and an amount of amino acid that is such that the amino acid to (Al+Zr) weight ratio is 2:1 to 1:20, preferably 1:1 to 1:10.

Further particularly preferred solid activated antiperspirant salt compositions, for example according to U.S. Pat. No. 6,902,723, include 48 to 78 wt. % (USP), preferably 66 to 75 wt. %, of an activated aluminum or aluminum-zirconium salt and 1 to 16 wt. %, preferably 4 to 13 wt. %, molecularly bound water, furthermore an amount of water-soluble strontium salt that is such that the Sr:(Al+Zr) weight ratio is 1:1 to 1:28, preferably 1:2 to 1:25, and an amount of glycine that is such that the glycine to (Al+Zr) weight ratio is 2:1 to 1:20, preferably 1:1 to 1:10.

Further particularly preferred solid activated antiperspirant salt compositions, for example according to U.S. Pat. No. 6,902,723, include 48 to 78 wt. % (USP), preferably 66 to 75 wt. %, of an activated aluminum or aluminum-zirconium salt and 1 to 16 wt. %, preferably 4 to 13 wt. %, molecularly bound water, furthermore an amount of water-soluble strontium salt that is such that the Sr:(Al+Zr) weight ratio is 1:1 to 1:28, preferably 1:2 to 1:25, and an amount of hydroxyalkanoic that is such that the hydroxyalkanoic acid to (Al+Zr) weight ratio is 2:1 to 1:20, preferably 1:1 to 1:10.

Further preferred activated aluminum salts are those of general formula $Al_2(OH)_{6-a}Xa$, where X is Cl, Br, I or $NO_3$, and "a" is a value from 0.3 to 5, preferably from 0.8 to 2.5, and particularly preferably 1 to 2, so that the molar ratio of Al:X is 0.9:1 to 2.1:1, as they are disclosed in U.S. Pat. No. 6,074,632, for example. In general, a small amount of hydration water is associatively bound in these salts, typically 1 to 6 moles of water per mole of salt. Aluminum chlorohydrate is particularly preferred (which is to say X is Cl in the aforementioned formula), and specifically 5/6 basic aluminum chlorohydrate, where "a" is 1, so that the molar ratio of aluminum to chlorine is 1.9:1 to 2.1:1.

Preferred activated aluminum-zirconium salts are those that represent mixtures or complexes of the above-described aluminum salts with zirconium salts of formula $ZrO(OH)_{2-pb}Y_b$, where Y is Cl, Br, I, $NO_3$ or $SO_4$, b is a rational number from 0.8 to 2, and p is the valence of Y, as they are disclosed in U.S. Pat. No. 6,074,632, for example. In general, a small amount of hydration water is likewise associatively bound in the zirconium salts, typically 1 to 7 moles of water per mole of salt. The zirconium salt is preferably zirconyl hydroxychloride of formula $ZrO(OH)_{2-b}Cl_b$, where b is a rational number from 0.8 to 2, preferably 1.0 to 1.9. Preferred aluminum-zirconium salts have an Al:Zr molar ratio of 2 to 10 and a metal:(X+Y) ratio of 0.73 to 2.1, preferably 0.9 to 1.5. A particularly preferred salt is aluminum-zirconium chlorohydrate (which is to say X and Y are Cl), which has an Al:Zr ratio of 2 to 10 and a metal:Cl molar ratio of 0.9 to 2.1. The term aluminum-zirconium chlorohydrate encompasses the tri-, tetra-, penta- and octa-chlorohydrate forms.

Preferred zirconium salts according to the invention have the general formula $ZrO(OH)_{2-a}Cl_a \cdot xH_2O$, where a=1.5 to 1.87, and x=1 to 7, wherein a and x are rational numbers. These zirconium salt are disclosed in the Belgium specification BE 825146, for example.

Further preferred active antiperspirant agents are disclosed in U.S. Pat. No. 6,663,854 and US 20040009133. The active antiperspirant ingredients can be present either in solubilized or else in undissolved, suspended form.

Unless the active antiperspirant ingredients are present suspended in a carrier that cannot be mixed with water, it is preferred for product stability reasons if the active ingredient particles have a number average particle size of 0.1 to 200 μm, preferably 1 to 50 μm, particularly preferably 3 to 20 μm, and exceptionally preferably 5 to 10 μm.

Preferred aluminum salts and aluminum-zirconium salts have a metal-to-chloride molar ratio of 0.9 to 1.3, preferably 0.9 to 1.1, particularly preferably 0.9 to 1.0.

Preferred aluminum-zirconium chlorohydrates in general have the empirical formula $Al_nZr(OH)_{[3n+4-m(n+1)]}(Cl)_{[m(n+1)]}$ where n=2.0 to 10.0, preferably 3.0 to 8.0, m=0.77 to 1.11 (corresponding to a metal (Al+Zr)-to-chloride molar ratio of 1.3 to 0.9), preferably m=0.91 to 1.11 (corresponding to M:Cl=1.3 to 0.9), and particularly preferably m=1.00 to 1.11 (corresponding to M:Cl=1.0 to 0.9), further very preferably m=1.02 to 1.11 (corresponding to M:Cl=0.98 to 0.9) and very preferably m=1.04 to 1.11 (corresponding to M:Cl=0.96 to 0.9).

In general, a small amount of hydration water is associatively bound in these salts, typically 1 to 6 moles of water per mole of salt, corresponding to 1 to 16 wt. %, preferably 4 to 13 wt. %, hydration water.

The preferred aluminum-zirconium chlorohydrates are usually associated with an amino acid to prevent polymerization of the zirconium species during production. Preferred stabilizing amino acids are selected from the group consisting of glycine, alanine, leucine, isoleucine, β-alanine, cysteine, valine serine, tryptophan, phenylalanine, methionine, β-amino-n-butyric acid and γ-amino-n-butyric acid, and the salts thereof, each in the D form, the L form, and the DL form, glycine being particularly preferred. The amino acid is present in the salt in an amount of 1 to 3 moles, preferably 1.3 to 1.8 moles, in each case per mole of zirconium.

Preferred antiperspirant salts are aluminum-zirconium tetrachlorohydratesi (Al:Zr=2 to 6; M:Cl=0.9 to 1.3), in particular salts having a metal-to-chloride molar ratio of 0.9 to 1.1, preferably 0.9 to 1.0.

Aluminum-zirconium chlorohydrate glycine salts that are stabilized with betaine (($CH_3$)$_3N^+$—$CH_2$—$COO^-$) are furthermore preferred according to the invention. Particularly preferred corresponding compounds have a total molar (betaine+glycine)/Zr ratio of (0.1 to 3.0): 1, preferably (0.7 to 1.5): 1 and a molar ratio of betaine to glycine of at least 0.001:1. Corresponding compounds are disclosed in U.S. Pat. No. 7,105,691, for example.

The active antiperspirant ingredients can be used in the form of non-aqueous solutions or in the form of glycolic solubilizates.

In a particularly preferred embodiment, the composition includes an astringent aluminum salt, in particular aluminum chlorohydrate, which is sold in powder form, for example, as Micro Dry® Ultrafine or Superultrafine from Reheis, Microdry 323 from Summit, as Chlorhydrol® and in activated form as Reach® 501 from Reheis. Reheis offers an aluminum sesquichlorohydrate under the designation Reach® 301, which is likewise particularly preferred. Activated aluminum chlorohydrates are also particularly preferred, which are available under the designations Reach® 101 and Reach® 103, AACH-7171 from Reheis or Summit. The use of aluminum-zirconium tetrachlorohydrex glycine complexes, which are commercially available, for example, from Reheis under the designation Rezal®36 GP from Reheis or AZG-364 or 369 from Summit, in activated form, or as Reach® 908, in powder form, can also be particularly preferred according to the invention.

Particularly preferred are aluminum-zirconium pentachlorohydrex glycine complexes (AAZG-3108 or AAZG-3110 from Summit), aluminum-zirconium tetrachlorohydex glycine complexes (AAZG-3111 from Summit) and/or aluminum-zirconium octachlorohydex glycine complexes (AAZG-3109, AAZG-531 or AAZG-531 D from Summit or Zirkonal® AP3G from BK Giulini).

It is essential that the composition according to the invention includes at least one oil.

The at least one oil is preferably used in the compositions according to the invention in an amount of 20 to 85 wt. %, more preferably 30 to 80 wt. %, particularly preferably 40 to 75 wt. %, and especially particularly preferably 50 to 70 wt. %.

An oil according to the invention shall be understood to mean a liquid substance that can be mixed in bidistilled water to less than 1 wt. % under normal conditions.

The composition according to the invention particularly preferably includes at least one volatile oil as the oil. It is preferred, in turn, if the volatile oils, based on the weight of the composition, are present in the composition according to the invention in a total amount of 30 to 80 wt. %, particularly preferably 40 to 75 wt. %, especially particularly preferably 45 to 70 wt. %.

According to the invention, volatile oil is understood to mean oils that have a vapor pressure of 0.01 kPa or more at 293.15 K.

Preferred oils according to the invention are selected from silicone oils, which also include, for example, dialkyl and alkyaryl siloxanes, such as cyclopentasiloxane, cyclohexasiloxane, dimethylpolysiloxane and methylphenylpolysiloxane, but also hexamethyldisiloxane, octamethyltrisiloxane and decamethyltetrasiloxane.

Volatile silicone oils and volatile non-silicone oils are particularly preferred volatile oils. Volatile silicone oils, which may be cyclic, such as octamethylcyclotetrasiloxane, decamethylcyclopentasiloxane and mixtures thereof, as they can be found in the commercial products DC 244, 245, 344 and 345 from Dow Corning, for example, are particularly preferred according to the invention. Volatile linear silicone oils are likewise particularly preferred, in particular hexamethyldisiloxane ($L_2$), octamethyltrisiloxane ($L_3$), decamethyltetrasiloxane ($L_4$), and arbitrary mixtures of two and three of $L_2$, $L_3$ and/or $L_4$, preferably mixtures such as those present, for example, in the commercial products DC 2-1184, Dow Corning® 200 (0.65 cSt) and Dow Corning® 200 (1.5 cSt) from Dow Corning.

Volatile silicone oils are excellently suited according to the invention since they give the composition according to the invention a pleasant skin sensation and low soiling of clothing. Particularly preferred compositions according to the invention are therefore characterized by a content of at least one volatile silicone oil. It is preferred, in turn, if the volatile silicone oils, based on the weight of the composition, are present in the composition according to the invention in a total amount of 20 to 80 wt. %, in particular 30 to 80 wt. %, particularly preferably 40 to 75 wt. %, especially particularly preferably 45 to 70 wt. %.

In addition or instead of the at least one volatile silicone oil, it is also possible for at least one volatile non-silicone oil to be present. Preferred volatile non-silicone oils are selected from $C_8$ to $C_{16}$ isoparaffins, in particular from isodecane, isododecane, isotetradecane, and isohexadecane, and mixtures thereof. C10-13 isoparaffin (commercial product Pionier 2094 from Hansen & Rosenthal, for example) is particularly suitable.

This at least one volatile non-silicone oil is also preferably present in a total amount of 20 to 80 wt. %, particularly preferably of 30 to 80 wt. %, and especially particularly preferably of 40 to 75 wt. %, in each case based on the total weight of the composition.

Due to the skin sensation and the stability of the resulting compositions, silicone oils are particularly preferred as the volatile oil over isoparaffins.

In addition to the aforementioned substances, typically referred to as volatile silicone oils, and in addition to the aforementioned volatile non-silicone oils, the compositions according to the invention can additionally include at least one non-volatile oil selected from among non-volatile silicone oils and non-volatile non-silicone oils.

Preferred non-volatile silicone oils are selected from higher molecular weight linear dimethylpolysiloxanes, commercially available, for example, under the designation Dow Corning® 190, Dow Corning® 200 Fluid having kinematic viscosities (25° C.) in the range of 5 to 100 cSt, preferably 5 to 50 cSt, or else 5 to 10 cSt, and Baysilon® 350 M having a kinematic viscosity (25° C.) of approximately 350 cSt.

Likewise preferred non-volatiles silicone oils according to the invention are selected from silicones of formula (Sil-1), where x is selected from integers from 1 to 20, preferably 1 to 3.

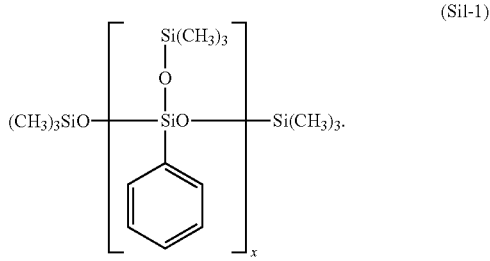

A preferred silicone oil of formula (Sil-1) is available under the INCI name Phenyl Trimethicone.

Natural and synthetic hydrocarbons, such as paraffin oils, $C_{18}$ to $C_{30}$ isoparaffins, in particular isoeicosane, polyisobutene or polydecene, which are available under the designation Emery® 3004, 3006, 3010 or under the designation Ethylflo® from Albemarle or Nexbase® 2004G from Nestle, for example, and 1,3-bis(2-ethylhexyl)cyclohexane (available under the trade name Cetiol®S from Cognis, for example) are likewise among the preferred non-volatile non-silicone oils according to the invention.

Further preferred non-volatile non-silicone oils according to the invention are selected from the benzoic acid esters of linear or branched $C_{8-22}$ alkanols. Particularly preferred are benzoic acid-$C_{12}$-$C_{15}$-alkyl esters, for example available as the commercial product Finsolv® TN, benzoic acid isostearyl esters, for example available as the commercial product Finsolv® SB, ethylhexyl benzoate, for example available as the commercial product Finsolv® EB, and benzoic acid 2-octyldodecyl esters, for example available as the commercial product Finsolv® BOD.

Further preferred non-volatile non-silicone oils according to the invention are selected from the triglycerides of linear or branched, saturated or unsaturated, optionally hydroxylated $C_{8-30}$ fatty acids. The use of natural oils can be particularly suitable, such as soy bean oil, cottonseed oil, sunflower oil, palm oil, palm kernel oil, linseed oil, almond oil, castor oil, corn oil, rapeseed oil, olive oil, sesame oil, safflower oil, wheat germ oil, peach kernel oil, and the liquid components of coconut oil, and the like. However, synthetic triglyceride oils are also suitable, in particular capric/caprylic triglycerides, such as the commercial products Myritol® 318 or Myritol® 331 (Cognis) or Miglycol® 812 (Hüls) comprising unbranched fatty acid esters and glyceryl triisostearyl and the commercial products Estol® GTEH 3609 (Uniqema) or Myritol® GTEH (Cognis) comprising branched fatty acid esters.

Further particularly preferred non-volatile non-silicone oils according to the invention are selected from the dicarboxylic acid esters of linear or branched $C_2$ to $C_{10}$ alkanols, in particular diisopropyl adipate, di-n-butyl adipate, di-(2-ethylhexyl) adipate, dioctyl adipate, diethyl-/di-n-butyl/di-octyl sebacate, diisopropyl sebacate, dioctyl malate, dioctyl maleate, dicaprylyl maleate, diisooctyl succinate, di-2-ethylhexyl succinate, and di-(2-hexyldecyl) succinate.

Further particularly preferred non-volatile non-silicone oils according to the invention are selected from among the esters of the linear or branched, saturated or unsaturated non-silicone oils, esters of unsaturated alkanols comprising 2 to 30 carbon atoms having linear or branched, saturated or unsaturated fatty acids having 2 to 30 carbon atoms, which can be hydroxylated. These include hexyldecyl stearate (Eutanol® G 16 S), hexyldecyl laurate, isodecyl neopentanoate, isononyl isononanoate, 2-ethylhexyl palmitate (Cegesoft® C 24) and 2-ethylhexyl stearate (Cetiol® 868). Likewise preferred are isopropyl myristate, isopropyl palmitate, isopropyl stearate, isopropyl isostearate, isopropyl oleate, isooctyl stearate, isononyl stearate, isocetyl stearate, isononyl isononanoate, isotridecyl isononanoate, cetearyl isononanoate, 2-ethylhexyl laurate, 2-ethylhexyl isostearate, 2-ethylhexyl cocoate, 2-octyldodecyl palmitate, butyloctanoic acid-2-butyl octanoate, diisotridecyl acetate, n-butyl stearate, n-hexyl laurate, n-decyl oleate, oleyl oleate, oleyl erucate, erucyl oleate, erucyl erucate, ethylene glycol dioleate, and ethylene glycol dipalmitate.

Further particularly preferred non-volatile non-silicone oils according to the invention are selected from the addition products of 1 to 5 propylene oxide units to monohydric or polyhydric $C_{8-22}$ alkanols, such as octanol, decanol, decanediol, lauryl alcohol, myristyl alcohol, and stearyl alcohol, such as PPG-2 myristyl ether and PPG-3 myristyl ether (Witconol® APM).

Further particularly preferred non-volatile non-silicone oils according to the invention are selected from the addition products of at least 6 ethylene oxide units and/or propylene oxide units to monohydric or polyhydric $C_{3-22}$ alkanols, such as glycerol, butanol, butanediol, myristyl alcohol and stearyl alcohol, which may optionally be esterified, such as PPG-14 butyl ether (Ucon Fluid® AP), PPG-9 butyl ether (Breox® B25), PPG-10 butanediol (Macol® 57), PPG-15 stearyl ether (Arlamol® E), and glycereth-7-diisononanoate.

Further particularly preferred non-volatile non-silicone oils according to the invention are selected from the $C_8$ to $C_{22}$ alkanol esters of monovalent or polyvalent $C_2$ to $C_7$ hydroxycarboxylic acids, in particular the esters of glycolic acid, lactic acid, malic acid, tartaric acid, citric acid, and salicylic acid. Such esters based on linear $C_{14/15}$ alkanols, such as $C_{12-15}$ alkyl lactate, and of $C_{12/13}$ alkanols branched at the 2-position, may be purchased under the trademark Cosmacol® from Nordmann, Rassmann GmbH & Co., Hamburg, in particular the commercial products Cosmacol® ESI, Cosmacol® EMI, and Cosmacol® ETI.

Further particularly preferred non-volatile non-silicone oils according to the invention are selected from the symmetrical, asymmetrical or cyclic esters of carbonic acid comprising alkanols, such as glycerol carbonate, dicaprylyl carbonate (Cetiol® CC) or the esters according to the teaching of DE 19756454 A1. Further oils that may be preferred according to the invention are selected from the esters of dimers of unsaturated $C_{12}$ to $C_{22}$ fatty acids (dimer fatty acids) comprising monohydric linear, branched or cyclic $C_2$ to $C_{18}$ alkanols or polyhydric linear or branched $C_2$ to $C_6$ alkanols.

It is preferred according to the invention if the compositions according to the invention, based on the total weight of the composition, include the non-volatile oils in a total amount of 0 to 20 wt. %, in particular of 0 to 10 wt. %.

It was found that the anhydrous compositions according to the invention can be thickened particularly well and in a stable manner when they include a mixture of specific lipophilic thickening agents as the thickening agent system.

It is therefore essential that the compositions according to the invention include a combination of the following lipophilic thickening agents:

at least one silicone elastomer;
at least one straight-chain or branched, saturated or unsaturated alcohol having more than 18 carbon atoms; and
at least one clay mineral mixture modified with quaternary ammonium groups.

Suitable silicone elastomers according to the invention shall preferably be understood to mean compounds that are obtainable by cross-linking an organopolysiloxane that includes at least 2 $C_2$ to $C_{10}$ alkenyl groups having a terminal double bond in each molecule with an organopolysiloxane that includes at least 2 silicone-bonded hydrogen atoms in each molecule.

Particularly preferred organopolysiloxanes according to the invention comprising at least 2 $C_2$ to $C_{10}$ alkenyl groups having a terminal double bond in the molecule are selected from methylvinylsiloxanes, methylvinylsiloxane-dimethylsiloxane copolymers, dimethylpolysiloxanes having dimethylvinylsiloxy end groups, dimethylsiloxane-methylphenylsiloxane copolymers having dimethylvinylsiloxy end groups, dimethylsiloxane-diphenylsiloxane-methylvinylsiloxane copolymers having dimethylvinylsiloxy end groups, dimethylsiloxane-methylvinylsiloxane copolymers having trimethylsiloxy end groups, dimethylsiloxane-methylphenylsiloxane-methylvinylsiloxane copolymers having trimethylsiloxy end groups, methyl-(3,3,3-trifluoropropyl)polysiloxanes having dimethylvinylsiloxy end groups, and dimethylsiloxane-methyl-(3,3,3-trifluoropropyl)-siloxane copolymers having dimethylvinylsiloxy end groups.

Particularly preferred cross-linking organopolysiloxanes according to the invention comprising at least two silicone-bonded hydrogen atoms are selected from methyl hydrogen polysiloxanes having trimethylsiloxy end groups, dimethylsiloxane-methylhydrogen siloxane copolymers having trimethylsiloxy end groups, and cyclic dimethylsiloxane-methylhydrogen-siloxane copolymers.

Particularly preferred silicone elastomers according to the invention, which, as raw material, are present already pre-swelled in a silicone that is liquid at room temperature under normal conditions and represent a silicone-based gel, are commercially available, for example under the trade name Corning 9040 Silicone Elastomer Blend (a cyclomethicone (and) dimethicone crosspolymer from Dow Corning; silicone elastomer content 12 to 13 wt. %), SFE 168, a cyclomethicone (and) dimethicone/vinyl dimethicone crosspolymer from GE Silicones, vinyl dimethicone crosspolymers, contained in KSG-15 (cyclomethicone (and) dimethicone/vinyl dimethicone crosspolymer, silicone elastomer content 4 to 10 wt. %), KSG-16 (dimethicone (and) dimethicone/vinyl dimethicone crosspolymer, silicone elastomer content 20 to 30 wt. %), KSG-17 (cyclomethicone (and) dimethicone/vinyl dimethicone crosspolymer), KSG-18 (phenyl trimethicone (and) dimethicone/phenyl vinyl dimethicone crosspolymer, silicone elastomer content 10 to 20 wt. %); and KSG-20, available from Shin Etsu Silicones of America (Akron, Ohio), and from Grant Industries Inc. (Elmwood Park, N.J.), the products from the Gransil® series, in particular Gransil SR-CYC (cyclomethicone and stearyl-vinyl/hydromethylsiloxane copolymer), Gransil® RPS Gel (INCI name: Cyclopentasiloxane and Polysilicone-11), Gransil® GCM-4 (INCI name: Cyclotetrasiloxane and Polysilicone-11), Gransil® GCM-5 (INCI name: Cyclopentasiloxane and Polysilicone-11), Gransil® RPS (INCI name: Cyclopentasiloxane and Polysilicone-11), GI-CD 10 (INCI name: Cyclopentasiloxane (and) Stearoxymethicone/Dimethicone Copolymer (and) Dimethicone), Gransil® IDS (INCI name: Isododecane (and) Cyclotetrasiloxane (and) Polysilicone-11), Gransil®PC-12 (INCI name: Isododecane (and) Polysilicone-11), Gransil®IDS-5 (INCI name: Isododecane (and) Cyclopentasiloxane (and) Polysilicone-11), Gransil®APK-1 (INCI name: Dimethicone and Cyclopentasiloxane and Polysilicone-11 and Nylon-12 and Methyl Methacrylate/Acrylonitrile Copolymer and PEG-10 Dimethicone and Polysorbate-40 and Isohexadecane and Ammonium Polyacryloyldimethyl Taurate), Gransil®DMCM-5 (INCI name: Dimethicone and Cyclopentasiloxane and Polysilicone-11), Gransil®DMG-6 with dimethicone (6 cSt) (INCI name: Dimethicone and Polysilicone-11), Gransil®DMG-20 with dimethicone (20 cSt) (INCI name: Dimethicone and Polysilicone-11), Gransil® AM-8 Gel (INCI name: Caprylyl Methicone and Cyclopentasiloxane and Polysilicone-11), Gransil® DM 5 with dimethicone (5 cSt) (INCI name: Dimethicone and Polysilicone-11), Gransil® DMID (INCI name: Dimethicone and Isododecane and Polysilicone-11), Gransil®PM (INCI name: Phenyl Trimethicone and Polysilicone-11), Gransil® ININ (INCI name: Isononyl Isononanoate (and) Polysilicone-11).

Silicone elastomers which, as raw material, are present already pre-swelled in a silicone that is liquid at room temperature under normal conditions, mixed with a non-silicone-containing oil, fat or wax, and represent a silicone-/non-silicone-based gel, can likewise preferably be used in the compositions according to the invention. Such silicone elastomer compositions are likewise commercially available, for example under the trade name Gransil® MLB (INCI name: Cyclopentasiloxane and Polysiliconel and Beeswax), Gransil® PS (INCI name: Cyclotetrasiloxane and Polysilicone-11 and Petrolatum), Gransil® PS-5 (INCI name: Cyclopentasiloxane and Polysilicone-11 and Petrolatum), Gransil® DMG-20 P with dimethicone (20 cSt) and petrolatum (INCI name: Dimethicone and Polysilicone-11 and Petrolatum), Gransil® RJO (INCI name: Cyclopentasiloxane and Polysilicone-11 and Jojoba Oil), Gransil® LANO (INCI name: Cyclopentasiloxane and Polysilicone-11 and Lanolin), Gransil® OHS-5 (INCI name: Cyclopentasiloxane and Polysilicone-11 and Octyl Hydroxystearate), and Gransil® DML (INCI name: Dimethicone (and) Neopentyl Glycol Diheptanoate (and) Polysilicone-11).

Preferred compositions according to the invention are characterized by having at least one silicone elastomer in a total amount of 0.05 to 3 wt. %, preferably 0.1 to 2.75 wt. %, particularly preferably 0.15 to 2.5 wt. %, exceptionally preferably 0.2 to 2 wt. %, in each case based on the total weight of the composition according to the invention.

The composition according to the invention includes at least one straight-chain or branched, saturated or unsaturated alcohol having more than 18 carbon atoms as the second component of the thickening agent mixture.

The at least one alcohol is preferably used in the compositions according to the invention in an amount of 0.5 to 10 wt. %, more preferably 1 to 8 wt. %, particularly preferably 1.5 to 7 wt. %, and especially preferably 2 to 6 wt. %, wherein the quantity information refers to the total weight of the compositions according to the invention.

It was found that optimal hardness of the soft solids and/or of the stick preparations can be achieved when straight-chain or branched, saturated or unsaturated alcohols (or alcohol mixtures) are used in the compositions according to the invention which preferably have a melting point in the range of 75 to 110° C., more preferably of 80 to 105° C., and particularly preferably of 85 to 100° C.

In a preferred embodiment, the compositions according to the invention include straight-chain or branched, saturated or unsaturated alcohols having more than 20 and fewer than 60 carbon atoms. Straight-chain, saturated alcohols having, on average, 20 to 40, preferably 25 to 35, and especially preferably having an average of 30 carbon atoms, are particularly preferred. Such alcohols are commercially available, for example under the trade name Performacol® 425 from Baker Petrolite.

The third essential component of the thickening agent mixture that the compositions according to the invention include is at least one clay mineral mixture modified with quaternary ammonium groups.

It was found that adding the clay mineral mixture increases the viscosity stability of the compositions according to the invention.

The clay mineral mixture modified with quaternary ammonium groups is preferably used in the compositions according to the invention, based on the total weight thereof, in an amount of 0.1 to 5 wt. %, more preferably 0.2 to 4 wt. %, particularly preferably 0.3 to 3 wt. %, and especially preferably 0.5 to 2.5 wt. %.

Preferred clay mineral mixtures within the meaning of the present invention include
  i) at least one clay mineral selected from sepiolite and/or palygorskite, and
  ii) at least one clay mineral of the smectite type.

These clay mineral mixtures are treated with quaternary ammonium compounds.

It was found that these special clay mineral mixtures modified with quaternary ammonium groups are superior to conventional clay mineral modified with quaternary ammonium groups (such as distearyldimonium hectorite), since they do not necessitate the additional presence of a polar activator (such as ethanol or propylene carbonate), which could not be incorporated into anhydrous compositions, or only with considerable difficulty, and be stabilized therein.

Clay minerals of type i) usually have a rod-shaped structure, while clay minerals of type ii) usually have a plate-shaped structure. By mixing clay mineral types i) and ii), non-uniform structures are achieved, which allow intermediate spaces to form in which active ingredients can be excellently suspended. It is further advantageous that the re-dispersion of the clay mineral mixture is prevented or minimized by the non-uniform structures, whereby the viscosity stability of the compositions according to the invention can be increased further.

Repelling, steric hindrances are created by the modification of the clay mineral mixture with quaternary ammonium group, the hindrances additionally supporting the dispersion of the clay mineral mixture.

Sepiolite (known as meerschaum; chemical formula $Mg_4Si_6O_{15}(OH)_2 \cdot 6H_2O$) and palygorskite (known as Mountain Leather; chemical formula $(Mg, Al)_2Si_4O_{10}(OH) \cdot 4H_2O$) are papyrus-like or fibrous magnesium silicates, which belong to the phyllosilicates. However, they differ from other phyllosilicates by the absence of continuous octahedral sheets.

Sepiolite is particularly preferred as clay mineral i) of the clay mineral mixture.

Suitable clay minerals according to the invention of the smectite type comprise clay minerals that include dioctahedral or trioctahedral structures and have plate-shaped structures.

The dioctahedral smectites include montmorillonite, beidellite, nontronite; the trioctahedral smectites include saponite, hectorite, stevensite and sauconite.

Synthetically produced smectites are likewise suitable according to the invention.

In a preferred embodiment, the clay minerals of the smectite type (ii) are therefore selected from hectorite, montmorillonite, bentonite, beidellite, saponite, stevensite, nontronite and/or sauconite.

In a particularly preferred embodiment, the clay minerals of the smectite type (ii) are therefore selected from hectorite, montmorillonite and/or bentonite, montmorillonite being particularly preferred.

In a further preferred embodiment, the clay minerals of types i) and ii) are mixed in such a way that the mixture preferably includes 50 to 95 wt. %, more preferably 60 to 95 wt. %, and especially preferably 70 to 90 wt. % of the clay mineral of type i), and 5 to 50 wt. %, preferably 5 to 40 wt. %, and in particular 10 to 30 wt. % of the clay mineral of type ii).

As previously described, the clay mineral mixture is modified with quaternary ammonium compounds. Suitable quaternary ammonium compounds for treating clay minerals and methods for treating clay minerals with such compounds are known.

Suitable quaternary ammonium compounds are preferably selected from quaternary alkylammonium salts of the following formula (I)

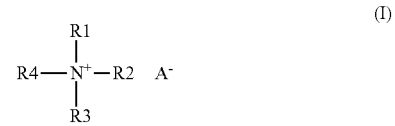

in which
R1 to R4 denote the same or different straight-chain, cross-linked, saturated or unsaturated C1 to C22 groups or benzyl groups, which may be substituted with one or more alkyl groups, and $A^-$ denotes a chloride, bromide, methylsulfate, nitrate, hydroxide, acetate and/or phosphate ion. Preferably at least one of the groups R1 to R4 is a straight-chain C1 to C4 alkyl group, preferably a methyl group, or a benzyl group, which may be substituted with one or more C1 to C4 alkyl groups, preferably with methyl groups.

$A^-$ preferably denotes a chloride, bromide or methylsulfate ion.

Examples of particularly preferred quaternary ammonium compounds with which the clay mineral mixture can be modified are dimethyl di(hydrogenated tallow) ammonium chloride, methylbenzyl di(hydrogenated tallow) ammonium chloride, dimethylbenzyl hydrogenated tallow ammonium chloride, dimethyl hydrogenated tallow-2-ethylhexylammonium chloride, and mixtures of these salts.

The clay mineral mixture is preferably treated with 5 to 80 milliequivalents (meq.) of the quaternary ammonium compound (per 100 g of the clay mineral mixture).

In a preferred embodiment, the clay mineral mixtures modified with quaternary ammonium compounds are produced by comminuting sepiolite and/or palygorskite, turned into a slurry with water and filtered so as to remove sand and other impurities. The clay mineral of the smectite type is also pretreated. The slurries of the clay minerals of types i) and ii) are further diluted with water (1 to 6% solids) and transferred into a high shear mill (for example, a Manton-Gaulin mill) so as to achieve homogenization. The slurry is optionally conducted several times through the high shear mill. Such a method is described in U.S. Pat. No. 5,160,454, for example, to which reference is made here.

Subsequently, the slurries of the clay minerals of types i) and ii) can be mixed, and the quaternary ammonium compound can be added. After dewatering, drying, and optionally comminuting the mixtures, a suitable clay mineral mixture c) according to the invention can be obtained.

Suitable clay mineral mixtures according to the invention that are modified with quaternary ammonium compounds are commercially available, for example from Southern Clay Products under the trade name Garamite®. Garamite® 7303 is a particularly preferred clay mineral mixture.

It was found that in particular soft solid products having excellent properties can be produced (syneresis<7.5%; hardness 0.015 to 0.045 mN) when the content of thickening agent c) is >0.5 wt. %, and thickening agent b) is used in excess compared to thickening agent a).

In a further particularly preferred embodiment, the content of thickening agent c) is thus at least 0.5 wt. %, based on the total weight of the composition, and the weight ratio of thickening agent b) to thickening agent a) is 7:1 to 100:1, preferably 8:1 to 50:1, and especially preferably 9:1 to 25:1.

Further preferred compositions according to the invention are characterized by additionally comprising at least one solid, water-insoluble particulate filler, for example so as to further improve the consistency and/or the sensory properties. In an exceptionally preferred embodiment, this filler is selected from optionally modified starches (such as of corn, rice, potatoes) and starch derivatives, which are pregelatinized if desired (such as Dry FLO PC from AKZO), silicon dioxide, silicic acids, such as Aerosil® types, spherical polyalkylsesquisiloxane particles (in particular Aerosil® R972 and Aerosil® 200V from Degussa), silica gels, talcum, kaolin, magnesium aluminum silicates, boron nitride, lactoglobulin derivatives, such as sodium $C_{8-16}$ isoalkylsuccinyl lactoglobulin sulfonate, available from Brooks Industries as the commercial product Biopol® OE, glass powders, polymer powders, in particular of polyolefins, polycarbonates, polyurethanes, polyamides, such as nylon, polyesters, polystyrenes, polyacrylates, (meth)acrylate or (meth)acrylate-vinylidene copolymers, which may be cross-linked, or silicones, and mixtures of these substances. Polymethacrylate copolymer-based polymer powders are available, for example, as the commercial product Polytrap® 6603 (Dow Corning). Other polymer powders, for example based on polyamides, are available under the designation Orgasol®1002 (polyamide-6) and Orgasol® 2002 (polyamide-12) from Elf Atochem. Further polymer powders suitable as preferred fillers according to the invention are, for example, polymethacrylates (Micropearl® M from SEPPIC or Plastic Powder A from NIKKOL), styrene-divinylbenzene copolymers (Plastic Powder FP von NIKKOL), polyethylene and polypropylene powders (ACCUREL® EP 400 from AKZO) or else silicone polymers (Silicone Powder X2-1605 from Dow Corning).

Preferred compositions according to the invention are characterized by comprising at least one solid, water-insoluble particulate filler in a total amount of 0.1 to 99 wt. %, preferably 0.2 to 90 wt. %, particularly preferably 0.3 to 15 wt. %, each based on the total composition.

Further preferred compositions according to the invention are characterized by comprising at least one scent and/or at least one perfume oil.

Individual odorous substance compounds, such as synthetic products of the ester, ether, aldehyde, ketone, alcohol, and hydrocarbon types, can be used as scents or perfume oils. Carvacrol, for example, is one of the phenolic odorous substance compounds. Odorous substance compounds of the ester type are, for example, benzyl acetate, methyl anthranilate, ortho-t-butylcyclohexyl acetate, p-tert-butylcyclohexyl acetate, diethyl phthalate, nonanediol-1,3-diacetate, isononyl acetate, isononyl formiate, phenylethyl phenylacetate, phenoxyethyl isobutyrate, linalyl acetate, dimethyl benzyl carbinyl acetate, phenylethyl acetate, linalyl benzoate, benzyl formiate, ethyl methylphenylglycinate, allyl cyclohexyl propionate, styrallyl propionate, benzyl salicylate, ethyl salicylate, isoamyl salicylate, hexyl salicylate, and 4-nonanolide. The ethers include, for example, benzyl ethyl ethers, the aldehydes include, for example, linear alkanals having 8 to 18 carbon atoms, citral, citronellal, citronellyl oxy acetaldehyde, cyclamen aldehyde, hydroxycitronellal, lilial and bourgeonal, the ketones include, for example, 6-acetyl-1,1,3,4,4,6-hexamethyltetrahydronaphthalene, para-t-amyl cyclohexanone, 2-n-heptyl cyclopentanone, β-methyl naphthyl ketone, and the ionones include α-isomethyl ionone and methyl cedryl ketone, the alcohols include cinnamon alcohol, anethol, citronellol, dimyrcetol, eugenol, geraniol, linalool, phenylethyl alcohol and terpineol, the hydrocarbons include 1,3,4,6,8-hexahydro-4,6,6,8,8-hexamethylcyclopenta-a-2-benzopyrane, hydroxymethyl isopropyl cyclopentane, 3a-methyl-dodecahydro-6,6,9a-trimethylnaphtho-2(2,1-b)furan, isobutyl quinoline, and the terpenes and balsams. Preferably, mixtures of different odorous substances are used, which together produce an appealing odorous note.

Suitable perfume oils can also include natural odorous substance mixtures such as those accessible from plant or animal sources, for example pine, citrus, jasmine, rose, lily or ylang ylang oil. Essential oils having lower volatility, which are usually used as aroma components, are also suitable as perfume oils, such as sage oil, chamomile oil, balm oil, mint oil, cinnamon leaf oil, lime blossom oil, juniper berry oil, vetiver oil, olibanum oil, galbanum oil, laudanum oil, clove oil, isoeugenol, thyme oil, bergamot oil, geranium oil, and rose oil.

Preferred compositions according to the invention include at least one scent and/or at least one perfume oil in a total amount of 0.01 to 10 wt. %, preferably 1 to 5 wt. %, particularly preferably 0.5 to 3 wt. %, exceptionally preferably 1 to 2 wt. %, in each case based on the total weight of the composition according to the invention.

In a preferred embodiment, the compositions according to the invention are formulated as soft solid antiperspirants. In this case, they can additionally include at least one active deodorant ingredient. Preferred such active deodorant ingredients are selected from odor absorbers, deodorizingly acting ion exchangers, antimicrobial substances, prebiotically active substances, and enzyme inhibitors, and particularly preferably combinations of the aforementioned active deodorant ingredients.

Silicates serve as odor absorbers, which advantageously also support the rheological properties of the composition according to the invention. The particularly advantageous silicates according to the invention include in particular phyllosilicates, and among these in particular montmorillonite, kaolinite, illite, beidellite, nontronite, saponite, hectorite, bentonite, smectite, and talcum. Further advantageous odor absorbers are, for example, zeolites, zinc ricinoleate, cyclodextrins, certain metal oxides, such as aluminum oxide, and chlorophyll.

Active antimicrobial ingredients according to the invention shall be understood as such active ingredients which reduce the number of odor-causing bacteria on the skin, or which inhibit growth of the same. These bacteria include, among other things, different species from the group of the staphylococci, the group of the *Corynebacterium*, anaerococci, and micrococci.

Preferred active antimicrobial ingredients according to the invention are in particular organohalogen compounds and organohalide compounds, quaternary ammonium compounds, a number of plant extracts, and zinc compounds. These include, among other things, triclosan, chlorhexidine and chlorhexidine gluconate, 3,4,4'-trichlorocarbanilide, bromochlorophene, dichlorophene, chlorothymol, chloroxylenol, hexachlorophene, dichloro-m-xylenol, dequalinium chloride, domiphen bromide, ammonium phenolsulfonate, benzalkonium halide, benzalkonium cetyl phosphate, benzalkonium saccharinate, benzethonium chloride, cetylpyridinium chloride, laurylpyridinium chloride, lauryl isoquinolinium bromide, methylbenzethonium chloride. Moreover, phenol, disodium dihydroxyethylsulfosuccinylundecylenate, sodium bicarbonate, zinc lactate, sodium phenolsulfonate and zinc phenolsulfonate, ketoglutaric acid, terpene alcohols, such as farnesol, chlorophyllin-copper complexes, α-monoalkylglycerol ethers having a branched or linear, saturated or unsaturated, optionally hydroxylated, $C_6$-$C_{22}$ alkyl group, particularly preferably α-(2-ethylhexyl) glycerol ether, commercially available as Sensiva® SC 50 (ex Schülke & Mayr), carboxylic acid esters of monoglycerol, diglycerol and triglycerol (such as glycerol monolaurate, diglycerol monocaprinate), lantibiotics, and plant extracts (such as green tea and components of lime blossom oil).

Further preferred active deodorant ingredients are selected from what are known as prebiotically acting components, which according to the invention shall be understood to mean such components which inhibit solely, or at least predominantly, the odor-causing bacteria of the skin microflora, but not the desired, which is to say not odor-causing bacteria that are part of a healthy skin microflora. The active ingredients disclosed as being prebiotically active in unexamined patent applications DE 10333245 and DE 10 2004 011 968 are explicitly included herein; among these are coniferous tree extracts, in particular from the group of the Pinaceae, and plant extracts from the group of the Sapindaceae, Araliaceae, Lamiaceae und Saxifragaceae, in particular extracts of *Picea* spp., *Paullinia* sp., *Panax* sp., *Lamium album* or *Ribes nigrum*, and mixtures of these substances.

The enzyme inhibitors include substances that inhibit the enzymes responsible for the decomposition of sweat, in particular the arylsulfatase, β-glucuronidase, aminoacylase, esterases, lipases and/or lipoxigenase, such as trialkyl citric acid esters, in particular triethyl citrate, or zinc glycinate. Preferred compositions according to the invention are characterized in that the at least one additional active deodorant ingredient is selected from arylsulfatase inhibitors, β-glucuronidase inhibitors, aminoacylase inhibitors, esterase inhibitors, lipase inhibitors, and lipoxigenase inhibitors, α-monoalkylglycerol ethers having a branched or linear, saturated or unsaturated, optionally hydroxylated $C_6$-$C_{22}$ alkyl group, in particular α(2-ethylhexyl)glycerol ether, prebiotically active components, trialkyl citric acid esters, in particular triethyl citrate, active ingredients that reduce the number of odor-causing bacteria on the skin, or inhibit growth of the same, from the group of the staphylococci, the group of the *Corynebacterium*, anaerococci, and micrococci, zinc compounds, in particular zinc phenolsulfonate and zinc ricinoleate, organohalogen compounds, in particular triclosan, chlorhexidine, chlorhexidine gluconate, and benzalkonium halides, quaternary ammonium compounds, in particular cetylpyridinium chloride, odor absorbers, in particular silicates and zeolites, sodium bicarbonate, lantibiotics, and mixtures of the aforementioned substances.

Further preferred compositions according to the invention are characterized in that the at least one additional active deodorant ingredient is present in a total amount of 0.1 to 10 wt. %, preferably 0.2 to 7 wt. %, particularly preferably 0.3 to 5 wt. %, based on the total weight of the active substance in the total composition.

Antioxidative substances can counteract the oxidative decomposition of the sweat components, and thereby inhibit odor development, in compositions according to the invention that are formulated as antiperspirants. Suitable antioxidants are imidazole and imidazole derivatives (such as urocanic acid), peptides such as D,L-carnosine, D-carnosine, L-carnosine and the derivatives thereof (such as anserine), carotinoids, carotenes (such as α-carotene, β-carotene, lycopene) and the derivatives thereof, lipoic acid and the derivatives thereof (such as dihydrolipoic acid), aurothioglucose, propylthiouracil and further thio compounds (such as thioglycerol, thiosorbitol, thioglycolic acid, thioredoxin, glutathione, cysteine, cystine, cystamine and the glycosyl, N-acetyl, methyl, ethyl, propyl, amyl, butyl, lauryl, palmitoyl, oleyl, γ-linoleyl, cholesteryl and glyceryl esters thereof) and the salts thereof, dilauryl thiodipropionate, distearyl thiodipropionate, thiodipropionic acid and the derivatives thereof (esters, ethers, peptides, lipids, nucleotides, nucleosides and salts) and sulfoximine compounds (such as buthionine sulfoximine, homocysteine sulfoximine, buthionine sulfone, penta-, hexa-, heptathionine sulfoximine) in very low compatible doses (such as pmol/kg to μmol/kg), furthermore metall chelators (such as α-hydroxy fatty acids, EDTA, EGTA, lactoferrin), humic acids, bile acid, gall extracts, catechins, bilirubin, biliverdin and the derivatives thereof, unsaturated fatty acids and the derivatives thereof (such as γ-linolenic acid, linoleic acid, arachidonic acid, oleic acid), folic acid and the derivatives thereof, hydroquinone and the derivatives thereof (such as arbutin), ubiquinone and ubiquinol and the derivatives thereof, vitamin C and the derivatives thereof (such as ascorbyl palmitate, stearate, dipalmitate, acetate, Mg-ascorbyl phosphate, sodium and magnesium ascorbate, disodium ascorbyl phosphate and sulfate, potassium ascorbyl tocopheryl phosphate, chitosan ascorbate), isoascorbic acid and the derivatives thereof, tocopherols and the derivatives thereof (such as tocopheryl acetate, linoleate, oleate and succinate, tocophereth-5, tocophereth-10, tocophereth-12, tocophereth-18, tocophereth-50, tocophersolan), vitamin A and derivatives (such as vitamin A palmitate), the coniferyl benzoate of benzoin resin, rutin, rutic acid and the derivatives thereof, disodium rutinyl disulfate, cinnamic acid and the derivatives thereof, kojic acid, chitosan glycolate and salicylate, butylhydroxytoluene, butylhydroxyanisole, nordihydroguaia resin acid, nordihydroguaiaretic acid, trihydroxybutyrophenone, uric acid and the derivatives thereof, mannose and the derivatives thereof, selenium and selenium derivatives (such as selenium methionine), stilbenes and stilben derivatives (such as stilbene oxide, trans-stilbene oxide). According to the invention, suitable derivatives (salts, esters, sugar, nucleotides, nucleosides, peptides and lipids) and mixtures of these active ingredients or plant extracts having these antioxidants can be used.

Tocopherol and the derivatives thereof, in particular tocopheryl acetate, and carotinoids and butylhydroxytoluene/butylhydroxyanisole are preferred as lipophilic, oil-soluble antioxidants from this group.

The total amount of the antioxidants in preferred preparations according to the invention that are formulated as antiperspirants is 0.001 to 10 wt. %, preferably 0.05 to 5 wt. %, and in particular 0.1 to 2 wt. %, based on the total preparation.

Complex-forming substances can also enhance the deodorizing action by complexing the oxidatively catalytically acting heavy metal ions (such as iron or copper) in a stable manner. Suitable complexing agents are selected from the complexing agents described above.

In a particularly preferred embodiment of the invention, the composition according to the invention is formulated as a cosmetic product, comprising:
i) a dispensing device, comprising:
   at least one container containing a piston that serves as cladding to the container and can be moved by a dispensing mechanism (in particular a nut-spindle system);
   at least one outlet opening, which is in fluid connection with said container; and
ii) a composition of the first subject matter of the invention present in said container.

The composition of the first subject matter of the invention can be discharged from the outlet opening of the dispensing device by actuation of the dispensing mechanism. This causes the piston to be moved, and the composition of the first subject matter of the invention to be pushed in the direction of the outlet opening. The resulting pressure drives said composition through the at least one outlet opening out of said dispensing device.

The anhydrous compositions according to the invention, especially those that are formulated as a soft solid, and in particular those that are formulated as a soft solid antiperspirant composition, have the advantage that they exhibit minimal syneresis (<7.5%) at optimal hardness (0.015 to 0.045 mN).

At the same time, they leave a dry, silky sensation on the skin, without leaving behind any residue whatsoever on clothing.

A second subject matter of the present application relates to the use of mixtures comprising:
at least one oil; and
a combination of thickening agents, comprising:
   a) at least one silicone elastomer;
   b) at least one straight-chain or branched, saturated or unsaturated alcohol having more than 18 carbon atoms; and
   c) at least one clay mineral mixture modified with quaternary ammonium compounds,
as a basis for cosmetic soft solid and/or stick preparations.

Preferred embodiments of the use according to the invention correspond to the preferred embodiments of the first subject matter of the invention.

The following examples are intended to illustrate the invention, without thereby limiting the invention to these examples. Unless noted otherwise, all quantity information refers to wt. % based on the total weight of the corresponding composition.

Examples

Variable components 1, 2 and 3 were mixed in the quantities indicated in the table (wt. %) with the following constant formulation components to form antiperspirants, until thickened soft solids had formed:
20 wt. % AAZG®[1] 531 D;
3.8 wt. % stearyl alcohol;
0.5 wt. % Aerosil®[2] 300;
65.7 wt. % Xiameter®[3] 0245.

| | Component 1 DC®[4] 9040 Silicone Elastomer Blend | Component 2 Garamite®[5] 7303 | Component 3 Performacol®[6] 425 | Syneresis [%] | Hardness [mN] |
|---|---|---|---|---|---|
| 1 | 4.50 | 0.00 | 5.50 | 9.1 | 0.012 |
| 2 | 4.13 | 1.68 | 4.19 | 7.1 | 0.028 |
| 3 | 5.43 | 0.00 | 4.57 | 6.7 | 0.007 |
| 4 | 3.89 | 1.02 | 5.09 | 4.9 | 0.035 |
| 5 | 4.97 | 2.00 | 3.03 | 9.0 | 0.018 |
| 6 | 6.00 | 0.88 | 3.12 | 12.5 | 0.008 |
| 7 | 5.12 | 0.96 | 3.92 | 11.8 | 0.010 |
| 8 | 3.42 | 0.58 | 6.00 | 6.8 | 0.017 |
| 9 | 2.00 | 2.00 | 6.00 | 4.2 | 0.037 |
| 10 | 3.01 | 2.00 | 4.99 | 4.7 | 0.034 |
| 11 | 6.00 | 2.00 | 2.00 | 8.4 | 0.013 |

1 INCI name: Aluminum Zirconium Octachlorohydrex GLY; 75 to 82 wt. % AS (Summit Research)
2 INCI name: Silica (Evonik Degussa)
3 INCI name: Cyclomethicone (Xiameter, Degussa)
[4]INCI name: Cyclomethicone, Dimethicone Crosspolymer; 12 to 12.75 wt. % elastomer content; Dow Corning
[5]INCI name: Quaternium-90 Sepiolite, Quaternium-90 Montmorillonite (Southern Clay Products)
[6]INCI name: C20-40 Alcohols (Baker Petrolite)

For the measurements of syneresis, 10 g of the respective product was placed in centrifuge tubes, incubated for 72 hours at 50° C., and subsequently centrifuged for 20 minutes at 3900 rpm.

The separated clear oil phases were removed in each case, weighed, and related to the total product.

For the determination of hardness, the force necessary to have a 30° cone penetrate 5 mm deep into the particular product matrix was ascertained in mN. This test was carried out with the TA.XT plus Texture Analyzer.

The test series were evaluated by way of the "Design Expert" and (see lines 2, 4, and 8 to 10 of the Table) show that certain compositions meet the target conditions (syneresis: <7.5%; hardness: 0.015 to 0.045 mN).

This applies in particular to compositions that include >0.5 wt. % Garamite®[5] 7303 and have a weight ratio of Performacol®[6] 425 to the silicone elastomer (AS in the commercial product DC®[4] 9040 Silicone Elastomer Blend) of at least 7:1.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:
1. An anhydrous composition, comprising:
at least one oil; and
a combination of thickening agents, comprising:
   a) at least one silicone elastomer;
   b) at least one straight-chain or branched, saturated or unsaturated alcohol having more than 18 carbon atoms; and c) 0.1 to 5 wt. %, based on the total weight of the composition, of at least one clay mineral mixture modified with quaternary ammonium compounds including
   i. at least one clay mineral selected from sepiolite and/or palygorskite, and
   ii. at least one clay mineral of the smectite type
wherein the thickening agent comprises at least 0.5 wt %, based on the total weight of the composition, and the weight ratio of thickening agents b):a) is 7:1 to 100:1.

2. The anhydrous composition according to claim 1, further comprising at least one active antiperspirant ingredient in an amount of 3 to 35 wt. %.

3. The anhydrous composition according to claim 1, wherein the active antiperspirant ingredient is selected from water-soluble astringent inorganic and organic aluminum, zirconium, zinc, salts thereof and combinations thereof.

4. The anhydrous composition according to claim 1, wherein the active antiperspirant ingredient is aluminum zirconium tetrachlorohydrex or octachlorohydrex glycine complexes.

5. The anhydrous composition according to claim 1, wherein the at least one oil comprises 20 to 85 wt. % based on the total weight of the composition.

6. The anhydrous composition according to claim 1, wherein the at least one oil comprises at least one volatile oil.

7. The anhydrous composition according to claim 1, wherein the at least one oil includes at least one volatile silicone oil.

8. The anhydrous composition according to claim 1, wherein the at least one silicone elastomer comprises 0.05 to 3 wt. % based on the total weight of the composition.

9. The anhydrous composition according to claim 1, wherein the at least one silicone elastomer comprises 0.2 to 2 wt. % based on the total weight of the composition.

10. The anhydrous composition according to claim 1, wherein the silicone elastomer is obtainable by cross-linking an organopolysiloxane that includes at least 2 $C_2$ to $C_{10}$ alkenyl groups having a terminal double bond in each molecule with an organopolysiloxane that includes at least 2 silicone-bonded hydrogen atoms in each molecule.

11. The anhydrous composition according to claim 1, the at least one straight-chain or branched, saturated or unsaturated alcohol having more than 18 carbon atoms comprises 0.5 to 10 wt. % based on the total weight of the composition.

12. The anhydrous composition according to claim 1, the at least one straight-chain or branched, saturated or unsaturated alcohol having more than 18 carbon atoms comprises 2 to 6 wt. % based on the total weight of the composition.

13. The anhydrous composition according to claim 1, wherein the at least one straight-chain or branched, saturated or unsaturated alcohol having more than 18 carbon atoms comprises a straight-chain, saturated alcohols having, on average, 20 to 40 carbon atoms.

14. The anhydrous composition according to claim 1, wherein the at least one clay mineral mixture modified with quaternary ammonium compounds comprises 0.5 to 2.5 wt. % based on the total weight of the composition.

15. The anhydrous composition according to claim 1, wherein the clay mineral of the smectite type is selected from hectorite, montmorillonite, bentonite, beidellite, saponite, stevensite, nontronite and/or sauconite.

16. The anhydrous composition according to claim 1, wherein the at least one clay mineral mixture modified with quaternary ammonium compounds comprises 50 to 95 wt. % of at least one clay mineral of the smectite type.

17. The anhydrous composition according to claim 1, wherein the at least one clay mineral mixture modified with quaternary ammonium compounds is modified with dimethyl di(hydrogenated tallow) ammonium chloride, methylbenzyl di(hydrogenated tallow) ammonium chloride, dimethylbenzyl hydrogenated tallow ammonium chloride, dimethyl hydrogenated tallow-2-ethylhexylammonium chloride, and mixtures of these salts.

\* \* \* \* \*